(12) United States Patent
Stevens

(10) Patent No.: US 9,192,361 B2
(45) Date of Patent: Nov. 24, 2015

(54) FECAL MICROBIOME TRANSPLANT MATERIAL PREPARATION METHOD AND APPARATUS

(71) Applicant: Christopher J Stevens, Houston, TX (US)

(72) Inventor: Christopher J Stevens, Houston, TX (US)

( * ) Notice: Subject to any disclaimer, the term of this patent is extended or adjusted under 35 U.S.C. 154(b) by 408 days.

(21) Appl. No.: 13/776,844

(22) Filed: Feb. 26, 2013

(65) Prior Publication Data

US 2014/0238154 A1    Aug. 28, 2014

(51) Int. Cl.
*A61B 10/00*    (2006.01)

(52) U.S. Cl.
CPC .................................. *A61B 10/0038* (2013.01)

(58) Field of Classification Search
None
See application file for complete search history.

(56) References Cited

U.S. PATENT DOCUMENTS

| 3,718,431 A | 2/1973 | Wild |
| 4,101,279 A | 7/1978 | Aslam |
| 5,316,732 A * | 5/1994 | Golukhov et al. ............ 422/527 |
| 2006/0122534 A1 | 6/2006 | Matsumura et al. |
| 2010/0291536 A1 * | 11/2010 | Viljoen et al. .................... 435/4 |
| 2011/0244461 A1 * | 10/2011 | Tanigami et al. ............ 435/6.11 |

\* cited by examiner

*Primary Examiner* — Robert R Raevis
(74) *Attorney, Agent, or Firm* — William M. Hobby, III

(57) ABSTRACT

This invention relates to a fecal microbiome transplant material preparation method and apparatus for the preparation of fecal material for a fecal transplant. A healthy patient's stool is collected and deposited in a first container which has its open end attached to a second container to form a fecal processing device. Blender blades are positioned in the second container and a filter is mounted therein. Liquid is injected into the second container through a syringe port having a valve therein to block the escape of liquid from the connected containers. Intake and exhaust ports allow air to enter and escape from the connected containers while blocking the escape of liquid. The liquid and fecal matter in the connected containers is blended and the blended liquid is strained through the filter in the second container and removed through the syringe port for use in a fecal transplant.

17 Claims, 4 Drawing Sheets

FECAL MICROBIOME TRANSPLANT MATERIAL PREPARATION METHOD AND APPARATUS

TECHNICAL FIELD

This invention is related to fecal microbiome transplants and especially to a method for the preparation of fecal material for a fecal transplant. Fecal microbiome transplants gather a fecal sample from a healthy donor to transplant into the GI tract of an ill recipient patient.

BACKGROUND OF THE INVENTION

The human gut microbiome is unique to each individual and can include more than a thousand different species. Disruptions to the homeostatic of the gut microbiome can play a role in inflammatory bowel diseases. Prior art treatments aimed at reshaping the microbial contents have used prebiotics, probiotics, and antibiotics and have generally failed to produce stable, long-term improvements in bacterial diversity. Fecal transplantation of gut microbiota from a healthy donor to an ill recipient in order to reconstitute the normal flora of a patient such as a *C. difficile* infected recipient is a more recent alternative.

Fecal microbiota transplants involves taking liquefied donor feces and transferring it to the patient such as during a colonoscopy. The patient receives a transplanted population of commensalistic bacteria that can combat the overgrowth of pathogenic bacteria. The donor is first tested for communicable infectious diseases. The donor then gives a stool sample which is mixed with a small amount of dilutant, such as sterile water or saline solution, which is blended by shaking the mixed material and then straining the blended material to separate some of the particulate material. A provider can then draw some of the liquid into a syringe for administering into the intestinal tract of a patient which can be accomplished with an endoscope, colonoscopy or enema.

U.S. Patent Application Publication No. 2006/0122534, to Matsumura et al. shows a container for suspension and filtration of stool material which enables a simple collection of cancer cells to be separated from the stool. The Aslam U.S. Pat. No. 4,101,279, is for a device for collecting and processing stool specimens. A specimen is collected with a bed pan or the like, which specimen is then put in a mixing bowl with a blender to blend the sample to obtain a sample for analysis. The Wild U.S. Pat. No. 3,718,431 is for a method of stool sample collection and testing for the presence of abnormalities such as occult, or hidden blood. A stool specimen is deposited in the device and onto a test medium and then allowed to pass down into the toilet.

The present invention is for an improved apparatus and method of processing fecal matter for a fecal transplant using a collection container which operatively connects to a second container to form an operative vessel for processing the specimen for a fecal transplant. A fecal microbiome transplant material preparation method and apparatus prepares fecal material for a fecal transplant. A healthy patient's stool is collected in a first container which has its open end attached to a second container's filter covered open end to form a fecal processing device. Liquid is injected into the second container through a syringe port having a valve therein to block the escape of liquid from the connected containers. Air intake and exhaust ports allow air displacement during injection and extraction of liquids from a closed system. The liquid and fecal matter in the connected containers is blended and the blended liquid is strained/filtered and removed through the syringe port for use in the fecal transplant.

SUMMARY OF THE INVENTION

This invention is related to fecal microbiome transplants and especially to a method for the preparation of fecal material for a fecal transplant. The process includes selecting a fecal processing apparatus having a fecal collection container having an open end and a fecal processing container having an open end. The fecal processing container has blending bars or blades covering the open end thereof and has a filter/strainer therein. The fecal processing container has a syringe port in the side thereof, which syringe port has a check valve therein, for the injection of and removal of materials. Fecal material is collected from a patient in the fecal collection container which then has its open end attached to the open end of the fecal processing container. An inert gas, such as nitrogen, may be injected into the sealed containers to protect anaerobic bacteria. A liquid, such as sterile water or a saline solution, is injected through the syringe port into the fecal processing container. The liquid and fecal material are then blended to facilitate breakdown of larger materials with the dilutant by shaking the connected containers which are reduced by the blades in the fecal processing container. The fecal processing container filter blocks some larger solids from entering into the liquefied fecal material reservoir in the processing container. The blended liquid material is then strained through the fecal processing container filter into the fecal material reservoir area of the fecal processing container and some of the blended material is removed from the fecal processing container with a syringe through the syringe port for use in a fecal transplant. Fecal material is thus collected and processed for use in a fecal microbiome transplant.

The apparatus for the preparation of fecal material for a fecal transplant has a first container having an open end for the collection of fecal matter from a donor. A second container, having an open end, is the fecal matter processing container for processing the fecal matter collected in the first container. The first and second containers are attached together with their open ends abutting to form a generally air and liquid tight seal therebetween. The second container has blending arms or blades over the opening and a screen filter therebelow. A syringe port has a valve therein to allow the injection of material therein and to prevent material from escaping therethrough when a syringe is not connected thereto. The second container has an air outlet port in the side thereof having a check or one-way valve therein to allow air to escape from said connected first and second containers when material is being added to the second container while limiting the escape of liquid from the connected first and second containers. The second container has an air inlet port having a check valve therein to allow air into the connected first and second containers when material is being removed from the containers while blocking the escape of air and liquid from exiting therethrough. Fecal matter collected in a first container is attached to the second container for processing using a syringe port in the second container to add and remove liquid from the connected containers.

BRIEF DESCRIPTION OF THE DRAWINGS

The accompanying drawings, which are included to provide further understanding of the invention are incorporated in and constitute a part of the specification, and illustrate an embodiment of the invention and together with the description serve to explain the principles of the invention.

In the drawings.

DETAILED DESCRIPTION OF EXEMPLARY EMBODIMENT

Figure 1:
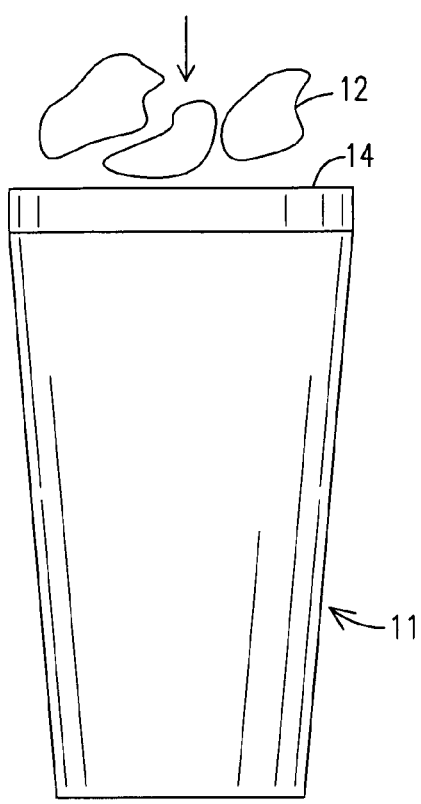
FIG. 1 is a side elevation of a stool collection container having fecal material being deposited therein.
Figure 2:
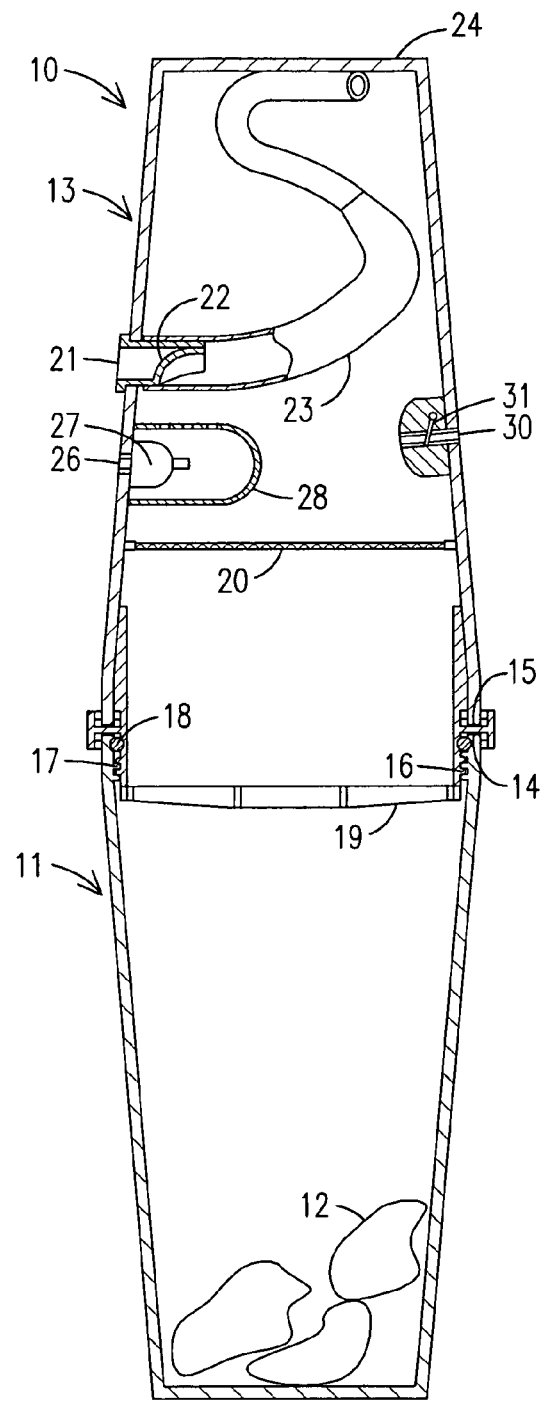
FIG. 2 is a sectional view of a fecal processor apparatus having the stool collection container attached thereto.

Referring to the drawings, FIGS. 1 and 2, a fecal microbiome transplant material processing apparatus 10 has a stool or fecal collection container or cup 11 having fecal material 12 being deposited therein in FIG. 1. The stool collection container 11 is shown attached to the fecal processing container 13 with the open end 14 of the stool collection container 11 attached to the open end 15 of the fecal processing container 13. The containers are attached with a threaded connection having internal threads 16 on the stool collection container 11 and external threads 17 on the fecal processing container 13. An O-ring seal 18 is used to seal the containers together in a liquid/airtight connection. It will however be clear that any other connection and seal can be used without departing from the spirit and scope of the invention. The fecal processing container 10 has blending arms or blades 19 forming a grid to blend and break down larger solid materials when shaking the fecal material with a dilutant, such as sterile water or a saline solution. The fecal processing container 10 also has a filter 20, such as a screen filter, attached across the opening 15 below the blending blades 19 to block the passage of solid fecal material in the stool collection container that is too large to pass through the screen filter 20. A syringe port 21 has a check or flap valve 22 therein to prevent escape of liquid material in the container 13. The syringe port 21 has a tapering tube connected thereto and extending into the container 13 bottom 29 (shown upside down in FIG. 2). The syringe port 21 can have a syringe 25, in FIG. 3, connected into the port 21 to open the valve 22 for injecting a liquid, such as sterile water, in a measured amount into the tube 23 and into the fecal processing container 13. Inert gas, such as nitrogen, can also be injected into the airtight apparatus 10 to protect anaerobic bacteria. The fecal processing container has an air exhaust opening 26 to allow the escapement of air when injecting fluid into the container with the syringe 25. The exhaust opening 26 has a check valve 27 to block air from entering through the port 26 and has an air filter 28 to filter the exhaust air. The check valve is closed when the apparatus is at rest and opens only during the pressurized injection of liquids into the fecal processing apparatus 10. The fecal processing container 13 has an air intake valve 30 having a check valve 31 therein to allow air into the container 13 when removing liquid with the syringe 25 while blocking the escape of air and liquids at other times.

Figures 3, 4:
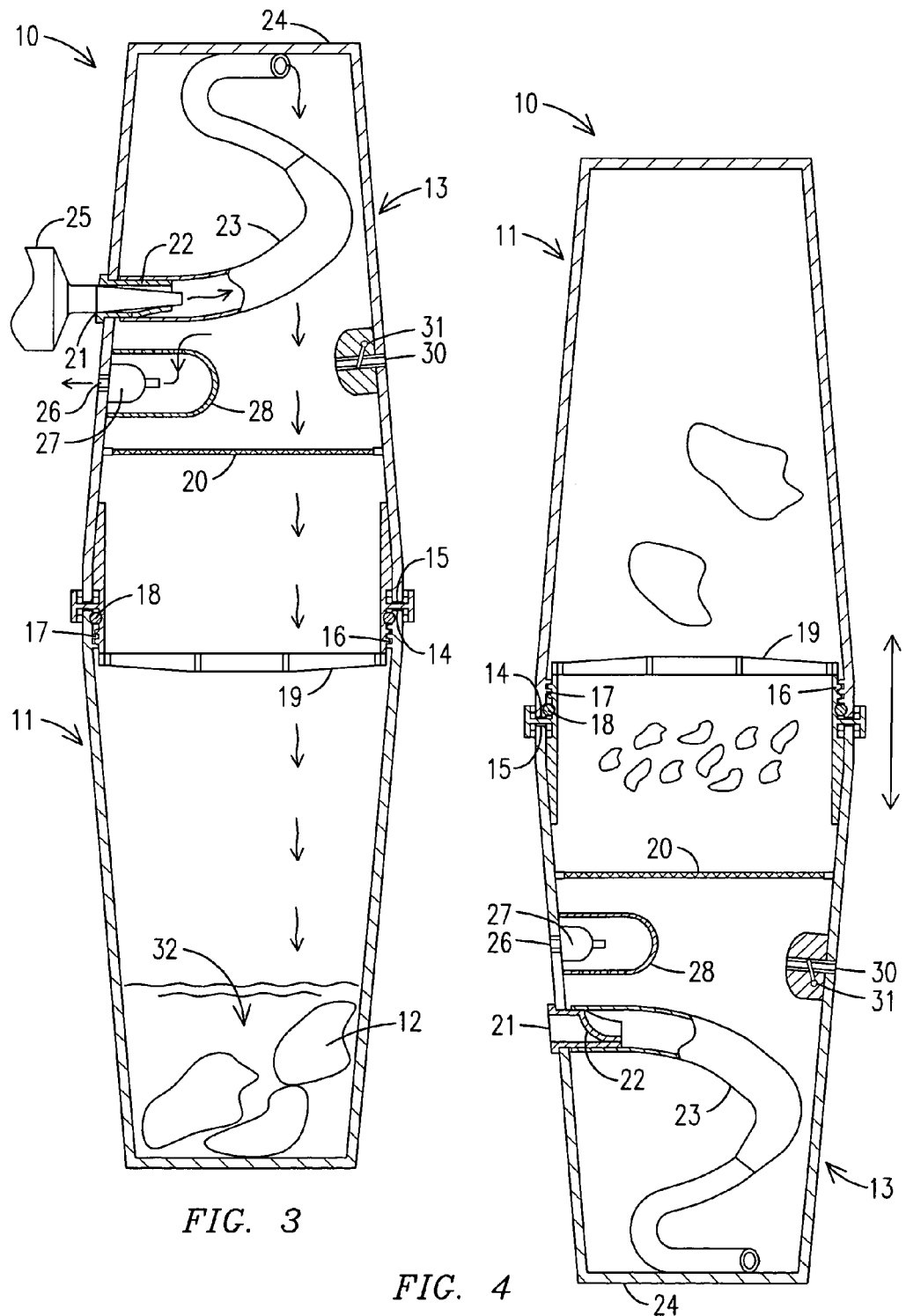
FIG. 3 is a sectional view of the fecal processor apparatus of FIG. 2 having a fluid injected thereinto.
FIG. 4 is a sectional view of the blending of the fecal material with the liquid therein.
Figures 5, 6:
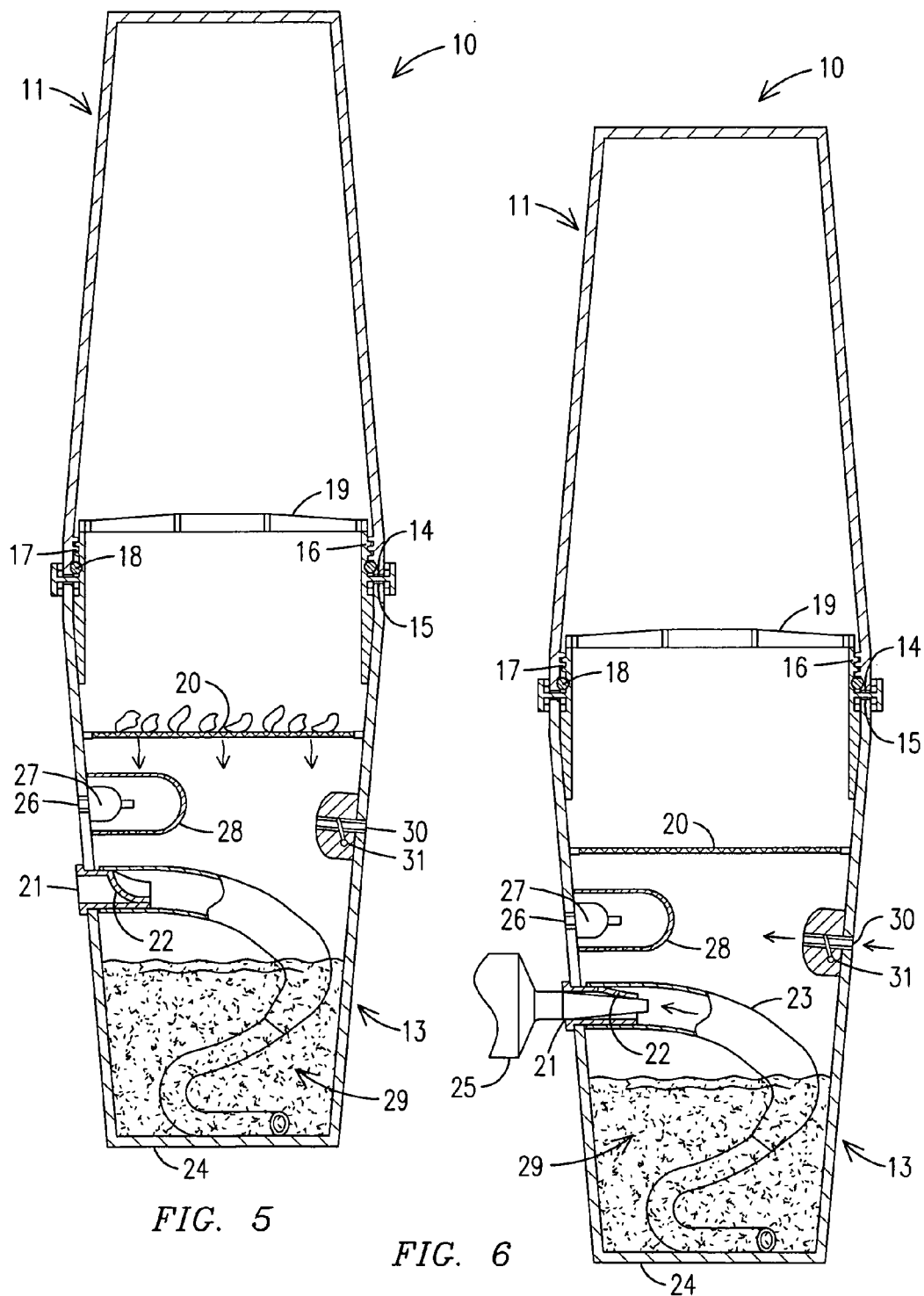
FIG. 5 is a sectional view of the blending of the fecal material with the liquid therein through the strainer in the fecal processor apparatus.
FIG. 6 is a sectional view of the fecal processor apparatus of FIG. 2 through 5 having the blended transplant fluid removed therefrom.
Figure 7:
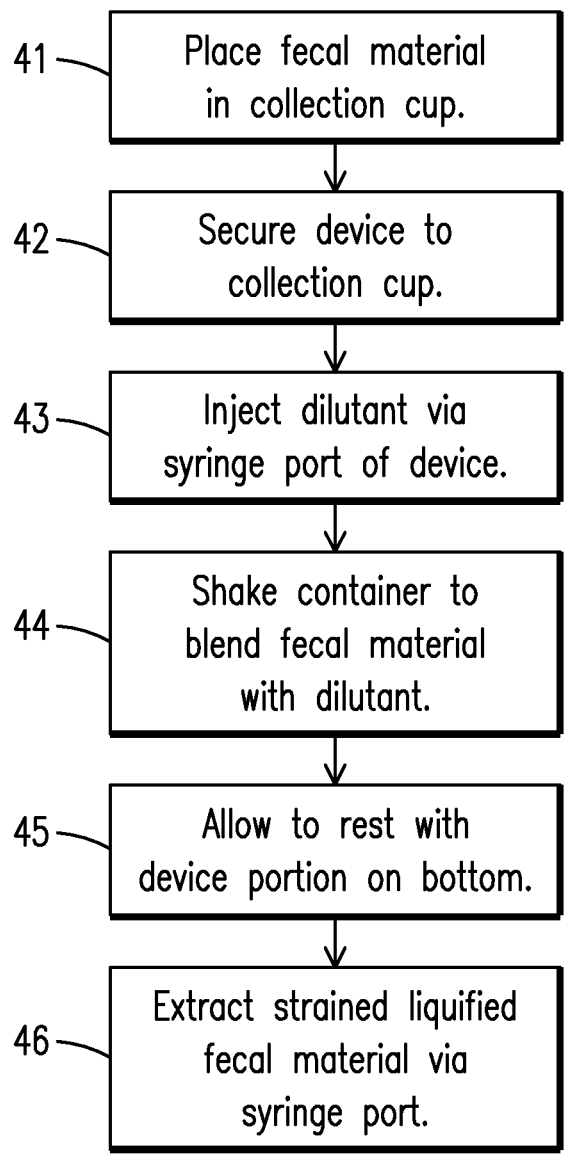
FIG. 7 is a flow diagram of the fecal microbiome transplant liquid preparation process in accordance with the present invention.

Referring to the drawings, FIGS. 1 through 7, the process (40) for the preparation of material for a fecal microbiome transplant is illustrated. In FIG. 7, the process starts with the step of collecting (41) fecal material 12 in the collection container 11 as shown in FIG. 1 and then attaching (42) or securing the container 11 with the fecal material 12 therein to the fecal processing container 13 with the threaded attachment using threads 16 and 17 having a seal 18 therein as shown in FIG. 2. A fluid, such as sterile water, is injected (43) into the connected containers for diluting the fecal material therein through the port 21 with a syringe 25 as shown in FIG. 3. An inert gas, such as nitrogen, can also be injected (39) into the apparatus 10 to protect the anaerobic bacteria. Shaking (44) the apparatus 10 having the fecal matter 12 and the diluted liquid 32 therein is shown in FIG. 4 to blend the fecal material with the dilutant, such as sterile water, while blocking larger solid material in the stool collection container therein by the screen filter 20. Settling (45) the blended liquid into the bottom 29 of the container 13 is accomplished by resting the apparatus 10 on the container 13 bottom 24. The blended liquid is then extracted (46) with the syringe 25 through the port 21 and tube 23. The tapering of the tube 23 reduces the volume of liquid in the tube when injecting a liquid into the container while the syringe 25 allows a carefully measured amount of liquid to be injected into the apparatus 10.

It should be clear at this time that a process and an apparatus for preparing fecal microbiome transplant material has been described in the specifications and drawings. However the present invention is not to be considered limited to the forms shown which are to be considered illustrative rather than restrictive.

I claim:

1. A method for the preparation of fecal material for a fecal transplant comprising the steps of:
    obtaining a fecal processing apparatus having a fecal collection container having an open end and a fecal processing container having an open end, said fecal processing container having a filter therein and having a syringe port in the side thereof for the injection of and removal of materials, said syringe port having a check valve therein to prevent the escape of liquids therethrough from said fecal processing container;
    depositing fecal matter from a patient into said fecal collection container;
    attaching the open end of said fecal collection container having fecal matter therein to the open end of the fecal processing container;
    injecting a dilutant liquid through the syringe port into said connected fecal processing container and fecal collection container;
    blending said injected liquid and collected fecal matter in said connected fecal collection container and fecal processing container and separating solid materials from passing through said fecal processing container filter;
    draining said blended liquid material through said fecal processing container filter into said fecal processing container; and
    removing material from said fecal processing container through said syringe port for use in a fecal transplant;
    whereby fecal material is collected and processed for use in a fecal transplant.

2. The method for the preparation of fecal material for a fecal transplant in accordance with claim 1 in which the step of obtaining a fecal processing apparatus includes a fecal processing container having blending blades therein.

3. The method for the preparation of fecal material for a fecal transplant in accordance with claim 2 in which the step of injecting a fluid into said processing apparatus includes injecting sterile water.

4. The method for the preparation of fecal material for a fecal transplant in accordance with claim 3 in which blending includes shaking the attached fecal collection container and fecal processing container to blend the materials therein passing through said blending blades.

5. The method for the preparation of fecal material for a fecal transplant in accordance with claim 4 in which the step of draining includes resting the fecal processing container below the attached fecal collection container to allow drainage into the fecal processing container through said filter.

6. The method for the preparation of fecal material for a fecal transplant in accordance with claim 5 in which the step of obtaining a fecal processing apparatus includes obtaining a fecal processing container having an air exhaust port having a filter and a check valve therein through the side thereof to allow air to escape therefrom when injecting liquids into said fecal processing apparatus.

7. The method for the preparation of fecal material for a fecal transplant in accordance with claim 6 in which the step of obtaining a fecal processing apparatus includes obtaining a fecal processing container having an air intake port having a check valve therein through the side thereof to allow air to be drawn into said container when removing liquids therefrom.

8. The method for the preparation of fecal material for a fecal transplant in accordance with claim 7 in which the step of obtaining a fecal processing apparatus includes obtaining a fecal processing container syringe port having an a tapered tube attached thereto, said tapered tube extending into the fecal processing container.

9. The method for the preparation of fecal material for a fecal transplant in accordance with claim 8 in which the step of obtaining a fecal processing apparatus includes obtaining a fecal processing container having a threaded surface around the open end thereof matching a threaded surface around the open end of the fecal collection container thereby allowing the containers to be threadedly connected together.

10. The method for the preparation of fecal material for a fecal transplant in accordance with claim 9 in which attaching the fecal processing container and the fecal collection container includes attaching a seal therebetween for forming an air and liquid tight seal therebetween.

11. The method for the preparation of fecal material for a fecal transplant in accordance with claim 1 including the step of injecting an inert gas into said fecal processing container.

12. The method for the preparation of fecal material for a fecal transplant in accordance with claim 11 in which said inert gas is nitrogen.

13. An apparatus for the preparation of fecal material for a fecal transplant comprising:
   a first container for the collection of fecal matter from a donor, said container having an open end; and
   a second container for processing the fecal matter collected in said first container, said second container having an open end, said first and second containers being removably attached together with their open ends abutting to form a generally airtight seal;
   said second container having blending blades and a filter therein and having a syringe port having a valve therein to allow the injection and the removal of a liquid therethrough with a syringe while preventing material from escaping therethrough when a syringe is not connected thereto, said second container having a gas outlet port in the side thereof having a valve therein to allow gas to escape from said connected first and second attached containers when material is being added to said second container, said second container having an air inlet port having a valve therein to allow air into said attached first and second containers when material is being removed therefrom through said syringe port while blocking fluid from escaping therethrough;
   whereby fecal matter collected in said first container attached to said second container can be processed for use in a fecal transplant.

14. The apparatus for the preparation of fecal material for a fecal transplant in accordance with claim 13 in which said first and second containers each has a threaded rim around the open ends thereof for attaching said containers together.

15. The apparatus for the preparation of fecal material for a fecal transplant in accordance with claim 14 in which a seal is mounted between said attached first and second containers.

16. The apparatus for the preparation of fecal material for a fecal transplant in accordance with claim 15 in which a tapered tube is attached to said syringe port for directing injected material into the bottom of said second container and for removing material from the bottom of said second container.

17. The apparatus for the preparation of fecal material for a fecal transplant in accordance with claim 16 in which the filter in said second container is a screen filter.

\* \* \* \* \*